United States Patent [19]

Hett

[11] 4,072,147

[45] Feb. 7, 1978

[54] RADIATION ENDOSCOPE

[75] Inventor: John H. Hett, Bradenton, Fla.

[73] Assignee: American Cystoscope Makers Inc., Stamford, Conn.

[21] Appl. No.: 663,683

[22] Filed: Mar. 4, 1976

[51] Int. Cl.² .............................................. A61B 1/06
[52] U.S. Cl. ................................ 128/006; 128/303.1; 128/395
[58] Field of Search ........................................ 128/3-9, 128/348, 398, 395, 396, 303.1, 303.17, 172.1, 407

[56] References Cited

U.S. PATENT DOCUMENTS

| 3,710,798 | 1/1973 | Bredemeier | 128/303.1 |
|---|---|---|---|
| 3,769,963 | 11/1973 | Goldman et al. | 128/303.1 |
| 3,796,220 | 3/1974 | Bredemeier | 128/303.1 |

Primary Examiner—Robert W. Michell
Assistant Examiner—Henry S. Layton

Attorney, Agent, or Firm—St. Onge, Mayers, Steward & Reens

[57] ABSTRACT

A radiation endoscope is described wherein a laser or other radiation source is employed for therapeutic purposes. Radiation energy may be accurately directed at a target in a body cavity with the use of a marking spot whose light energy is passed along an optical path in the sheath of the radiation endoscope to the cavity area on which the radiation beam is incident. Eye protection for an operator of the radiation endoscope is obtained with the use of a variable filter interposed in an image path and coupled to correspondingly reduce the beam radiation effective in the body cavity as the image path transmissivity is enhanced. In one embodiment, attenuation of beam radiation is obtained by using a variable density optical filter coupled to the filter operative in the image path. In another embodiment, radiation beam attenuation is achieved by deriving a radiation beam control signal from the filter operative in the image path.

7 Claims, 6 Drawing Figures

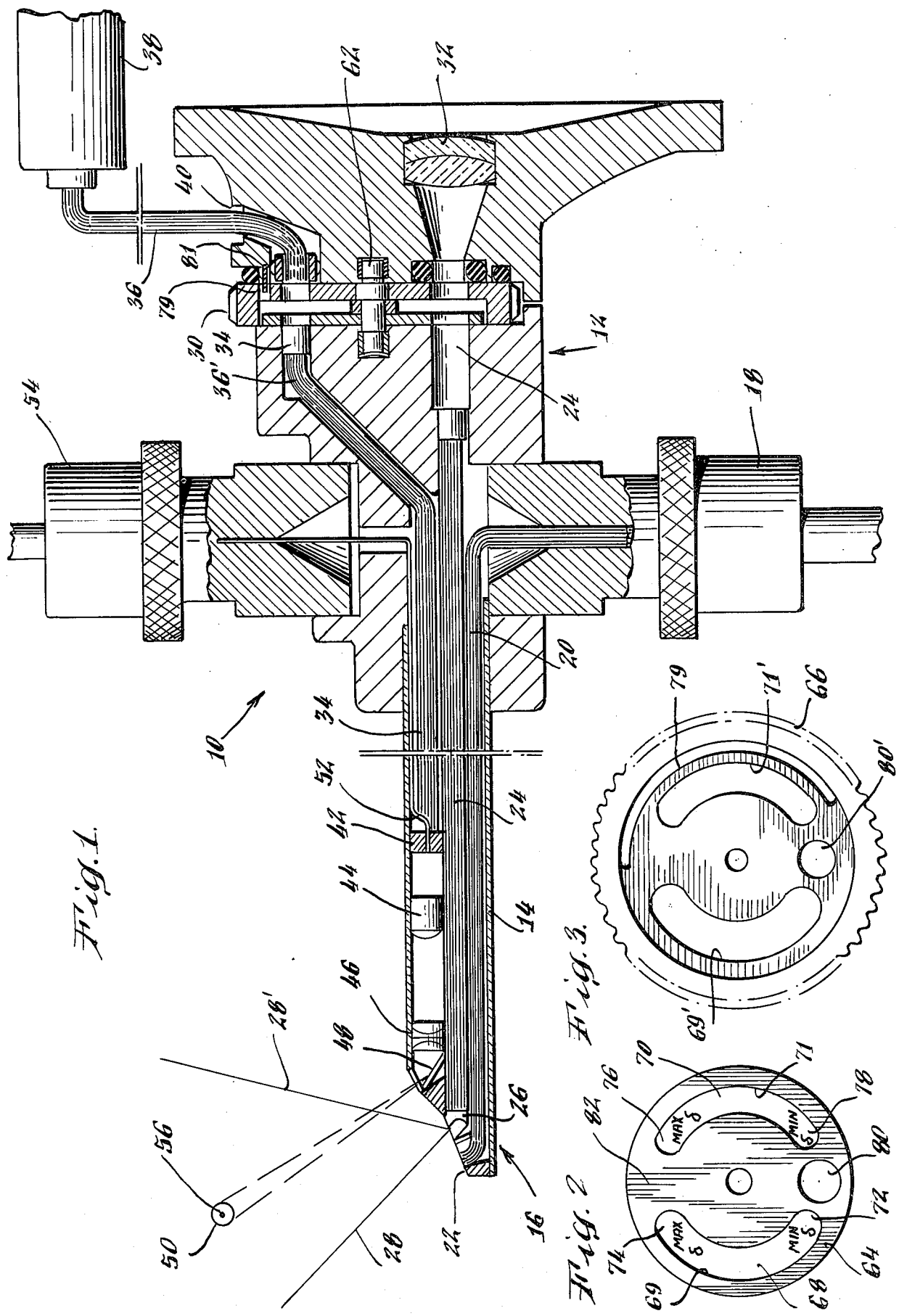

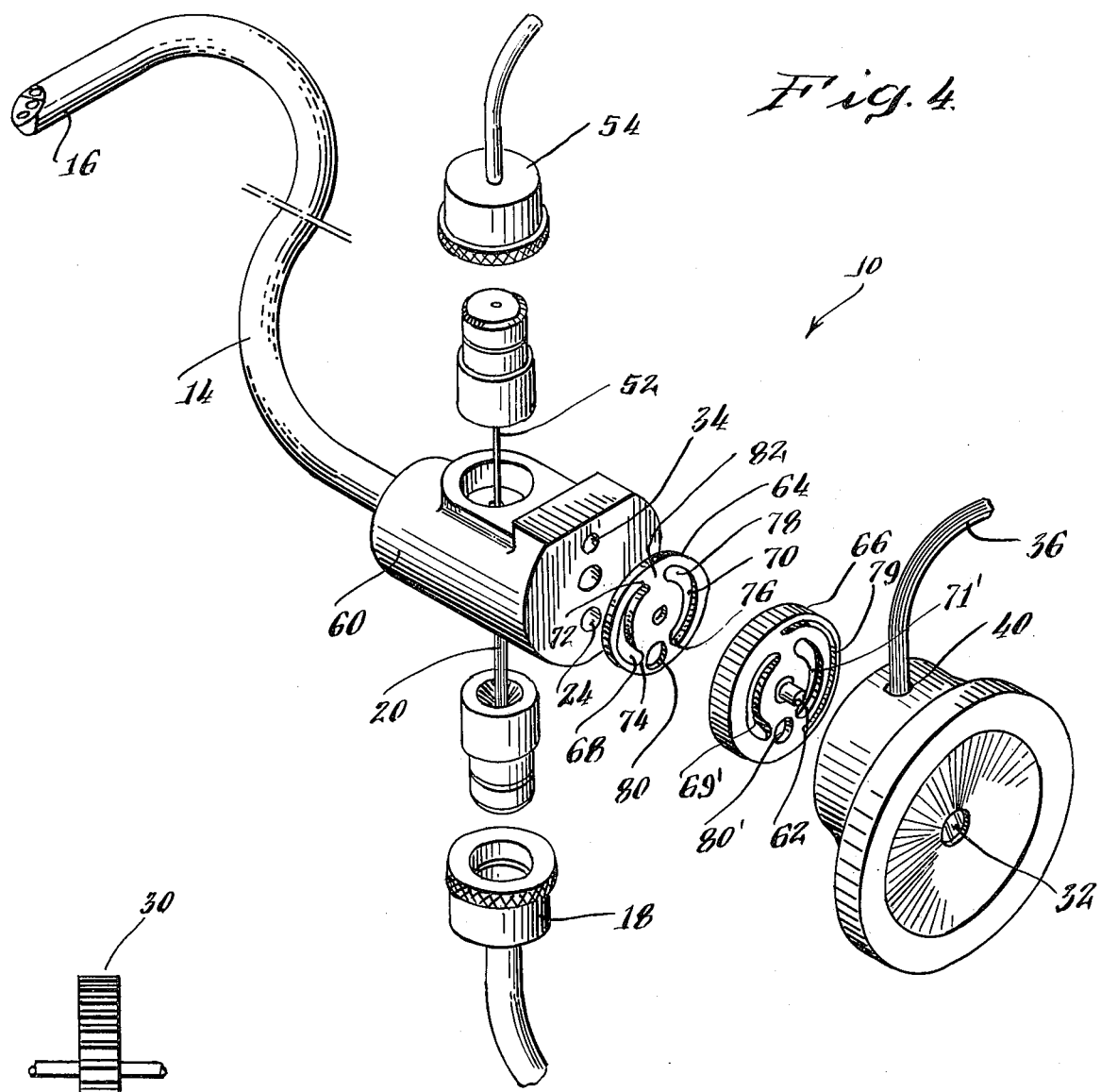
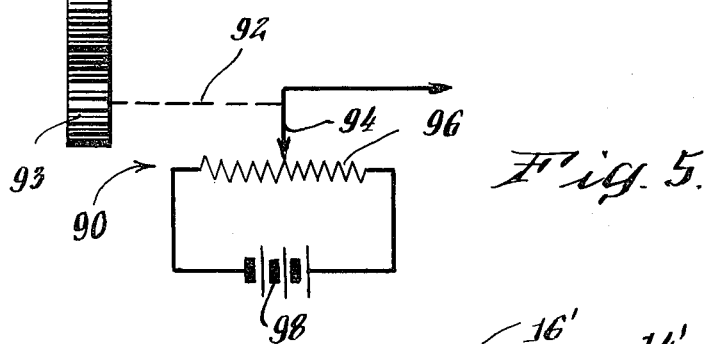
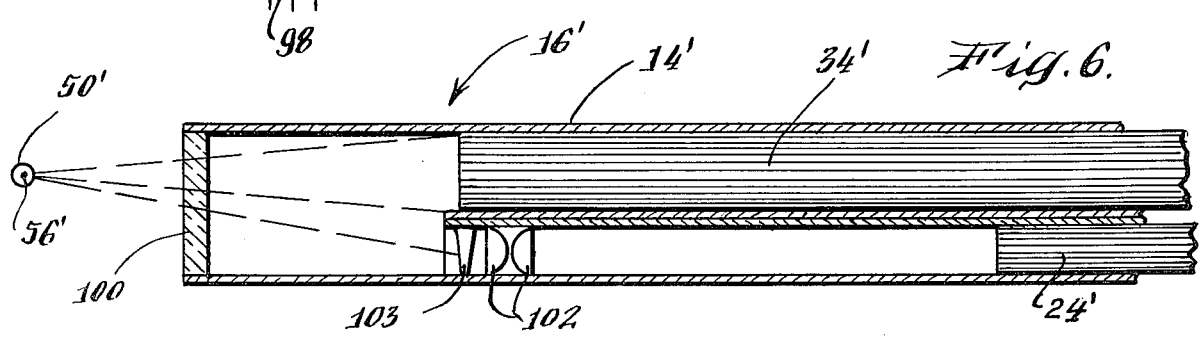

RADIATION ENDOSCOPE

FIELD OF THE INVENTION

This invention relates to endoscopes. More specifically, this invention relates to an endoscope utilizing laser or other high intensity radiation energy source.

BACKGROUND OF THE INVENTION

The use of laser energy for therapeutic purposes has been proposed. Note, for example, an article entitled "Experimental Examinations on Laser Endoscopy" by Frühmorgen et al, published in *Endoscopy* 6 (1974) at pages 116–122.

In the U.S. patent to Bass et al, U.S. Pat. No. 3,858,577, a flexible endoscope with a laser is described for performing laser surgery. The endoscope includes a sheath in which a plurality of optic fiber bundles are included. Another single optic fiber is provided to carry laser energy at a magnitude sufficient for therapeutic purposes.

In the U.S. patent to Bredemeier, U.S. Pat. No. 3,710,798 a laser system for microsurgery is described. A complex laser marking device is disclosed to indicate when the operating site is at the focal point of a converging operating laser beam.

Therapeutic employment of laser energy may involve laser light of different wavelengths. The argon laser, which is found to be particularly useful for blocking coagulation, produces energy in the visible spectrum. Observation of the impact point of a laser, when employed in an image transmitting endoscope, however, may result in an excessive, harmful exposure of the observer's eye.

When a laser or other radiation source is used whose energy is not in the visible region, care is needed to assure that high radiation energy cannot inadvertently become incident on the eye of an endoscope user. Such incidence is unlikely when the image transmitting path attenuates the laser beam. For example, the image transmitter may be a fiber optic bundle which is formed of a glass which attenuates the laser energy. There are, however, situations in which the attenuating fiber optic image bundle does not provide adequate attenuation such as in short endoscopes or when image transmitter paths with conventional optical elements are used.

When lasers or other high energy sources of invisible wavelengths are employed in an endoscope, care must be exercised that the emerging radiation beam impinges on the proper target of the body cavity. The targeting of a laser beam may involve a marking apparatus such as described in the Bredemeier patent. In an endoscope application, however, such marker is cumbersome and not conveniently suitable.

SUMMARY OF THE INVENTION

In one form for a radiation endoscope in accordance with the invention, eye protection is provided with an adjustable filter interposed in a laser path and image transmitter. A laser beam spotter is employed to enable one to target the therapeutic laser beam precisely on a segment of the body cavity being investigated.

With a radiation endoscope in accordance with the invention, radiation of different wavelengths outside the visible spectrum may be employed.

It is, therefore, an object of the invention to provide a radiation endoscope for therapeutic purposes. It is a further object of the invention to provide an eye protecting radiation endoscope suitable for therapeutic use with radiation of different wavelengths.

These and other objects and advantages of a radiation endoscope in accordance with the invention can be understood from the following description of an embodiment described in conjunction with the drawings.

BRIEF DESCRIPTION OF DRAWINGS

FIG. 1 is a longitudinal section of a radiation endoscope in accordance with the invention;

FIGS. 2 and 3 are plan views of filter segments employed with an endoscope shown in FIG. 1;

FIG. 4 is a perspective exploded view of the radiation endoscope shown in FIG. 1;

FIG. 5 is a schematic representation of an eye protection control device in a radiation endoscope in accordance with the invention; and FIG. 6 is a section view of the distal end of another form for a radiation endoscope in accordance with the invention.

DETAILED DESCRIPTION OF DRAWINGS

With reference to FIG. 1, a radiation endoscope 10 is shown. The radiation endoscope may be adapted for use in a broad range of applications such as a cystoscope, coloscope and the like. The technology of endoscopes has been well developed and the particular modifications needed to adopt the endoscope for investigation of a specific body cavity are well known.

The radiation endoscope 10 is formed with an optical head 12 at a proximal end and a sheath 14 extending away therefrom to a distal end 16. The sheath 14 may be a rigid enclosure or a flexible type as are well known in the art. The sheath may be round or ovoid in crossection or have such other shape as may appear desirable for the particular purpose intended for the laser endoscope.

The radiation endoscope 10 includes a plurality of separate optical paths extending between the proximal and distal ends. An illuminating light path is provided to carry light from a suitable source (not shown) through a light coupler 18 and a fiber optic bundle 20 to the distal end 16. The illumination light bundle 20 terminates at a suitable end surface 22 in a manner permitting illumination of a broad field generally extending laterally and forward of the distal end 16. The distal end surface 22 is sealed against body fluids by, for example, providing a suitable transparent protective cover (not shown).

An image transmitter 24 is provided in the form of a fiber optic bundle and extends from the distal end 16 to the optical head 12. The image transmitter 24 may include a suitable lens, such as 26, to provide a lateral field of view as delineated by lines 28–28' in a manner well known to the art of making endoscopes. The image transmitter 24 passes through a variable density filter 30 in the optical head 12 and terminates with an eyepiece 32.

A therapeutic radiation beam path 34 is provided in the form of a fiber optic bundle 36 which is coupled to a laser or other high energy source 38. The path 34 may be formed of a single fiber as shown in the patent to Bass et al. The fiber optic bundle 36 extends through an opening 40 in optical head 12 to the variable density filter 30. The therapeutic laser beam path 34 continues on the other side of filter 30 with a fiber bundle 36' which terminates in a fused silica retainer 42.

A suitable field lens 44 is aligned with the ends of the therapeutic fiber optic bundle 36' to collect the laser energy and apply a therapeutic laser beam through an objective 46 and via a reflector 48 to an image area 50. The image is located in a predetermined segment of the field of view as delineated by lines 28–28'.

The fused silica retainer 42 has a centrally located hole of a small diameter sufficient to receive a spotter light fiber or bundle 52. The fiber bundle 52 runs from the retainer 42 back to a separately controlled visible light source (not shown) through a standard fiber optic connector 54. The diameter of the spotter bundle 52 is selected to cause the generation of a visible marking light spot 56 in the center of image area 50 of the therapeutic laser beam.

At the proximal end both the therapeutic laser energy and the reflected image light are passed through adjustable filter 30. The filter is mounted for rotation to housing 60 with an axle 62. The filter 30 is formed of two parts, back-located filter 64 and a carrier 66, which are connected together for rotation as a unit about an axle 62. The interconnection of the filter 64 and carrier 66 may be by friction fit with axle 62 or in another suitable attaching manner.

As shown in FIGS. 2, 3 and 4, the filter 64 carries two filters, an image filter 68 in the form of a plate and a therapeutic radiation filter plate 70 respectively, mounted in slots 69, 71 to enable insertion in the image light path 24 and the therapeutic laser radiation path 34. Both the image filter 68 and therapeutic radiation filter 70 are formed with a variable density, $\delta$, filter plate such as may be formed by evaporating Inconel on a disc of fused silica. The filters are preferably formed on quartz plates which are polished flat to about $\frac{1}{4} \lambda$ on both sides with an overall thickness of about $1\frac{1}{2}$ millimeters.

The evaporation is deposited with a density gradient so that rotation of the filter 64 past the observer beam path 24 will result in variation of transmission of observable light from a minimum to a maximum value. For example, the counter clockwise rotation of filter 30 to a position where end segment 72 of image filter 68 is opposite the image light path 24 may correspond to the region of lowest density, $\delta$, of the filter. The opposite end segment 74 of filter 68 may then correspond with a maximum density region of the filter backplate 64. In a corresponding manner, the filter 70 may be a variable density filter whose maximum density region 76 is interposed in the laser path 34 when an observer requires maximum image intensity.

A transparent aperture 80 is provided in filter 64 and is diametrally opposite to a complete opaque region 82 between the ends 72, 78 of filter 68, 70. The aperture 80 may be rotated in alignment with the image path 24 while the opaque region 82 fully blocks the laser path 34. In this manner an image may be observed without obstruction by rotating filter 30.

The carrier 66 is formed in a similar manner as the filter 64 but with slots instead of filters. The slots are located for free passage of light through the various light paths 24, 34 as suggested by the use of similar but primed numerals. In addition, the carrier 66 is provided with a knurled peripheral edge. A slot 79 is milled into carrier 66 to receive a pin 81 mounted in head 12 as shown in FIG. 1. Pin 81 serves to limit rotational movement of filter 30. The filters 68, 70 may be of different gradients and materials chosen for the wavelength and intensity of the radiations used. Accurate alignment of the therapeutic radiation path is employed at the filter 30 to reduce energy losses. The filter 30 is mounted for quick replacement.

With a radiation endoscope 10 one may accurately locate the laser impact point. The operator merely needs to reduce the intensity of the illumination provided along the path 20 and increase the intensity of the spot light. When the spot light is on the tissue target, the laser beam can be actuated to perform its therapeutic function.

The radiation endoscope 10 provides eye protection by virtue of the variable filter 30. In another form, the variable movable filter may be mechanically linked to a control signal generator 90, see FIG. 5. The linkage is selected in a manner whereby a control signal is produced whose magnitude is related or proportional to the amount of filtering interposed in the image transmitter path 24. The control signal may then be used to control the operation of the laser source 38 such as its intensity. In such case therapeutic radiation filters 70, 70' need not be placed in the laser path 34. One advantage of the laser attenuation approach of FIG. 5 lies in that the laser path 34 may be formed of a continuous laser fiber 94 bundle extending without interruption from the distal end 16 to the laser source 38.

FIG. 5 illustrates an arrangement for generating a control signal representative of the desired safe intensity level for the radiation energy. A linkage 92, including a gear 93, is coupled between the adjustable filter 30 and wiper arm 94 of a potentiometer 96. The fixed terminals of the latter are connected across a fixed voltage source 98 to produce a control voltage on the wiper arm in proportion to the rotational position of the filter 30 relative to the image transmitter 24.

The control voltage on wiper arm 94 can be connected to a suitable control circuit in the laser source 38 to control the magnitude of the laser energy. For example, the laser response to the control voltage may be so set that a minimum or no laser power occurs when the control voltage magnitude corresponds to a filter position within a high range of transmissivity for the image path 24. In this manner the observer's eye is fully protected against high reflected laser radiation passing through the image path 24.

Having thus described a radiation endoscope in accordance with the invention, variations of the apparatus may be contemplated. For example, one may wish to investigate the segments of a body cavity directly in line with the longitudinal direction of the endoscope. FIG. 6 illustrates an example of the distal end 16' for a radiation endoscope wherein a direct forward view of a body cavity can be made. The endoscope's laser beam path 34' is shown to terminate before a transparent window 100. The optical fibers employed in path 34 may be of the graded index type. In the embodiment of FIG. 6, graded index rods can provide an image 50' in a particular forward location relative to window 100. Fiber bundle 24' with wedge 103 and objective system 102 constitute the image system. The energy is supplied through a graded index rod 34' with a centrally located marker (not shown) but such marker may be of the type as shown at 52 in FIG. 1. Other optical paths as described are provided through not visible in the view of FIG. 6. One may further appreciate that the radiation endoscope may be provided with such other channels as may be required for carrying water, special tools or for removing waste materials.

What is claimed is:
1. A radiation endoscope comprising an endoscopic sheath having a proximal end and a distal end and sized to investigate a body cavity, said endoscopic sheath enclosing
  a. an optical image transmitter extending from the proximal end of the endoscope sheath to its distal end to enable visual observation of a segment of the internal body cavity,
  b. a therapeutic energy carrying optical path in the form of a fiber optical bundle selected to transmit radiation energy of a predetermined therapeutic wavelength and a therapeutic power, said optical fiber bundle extending between the proximal and distal ends of the endoscopic sheath, the therapeutic energy carrying optical fiber bundle being selected and sized to enable a therapeutic radiation beam to emerge from the distal end, said therapeutic energy carrying optical fiber bundle further being selected to direct the emerging therapeutic radiation beam for incidence at a predetermined location relative to the distal end for treatment of the visually observable segment of the body cavity, and
  c. a spotter light path in the form of a light carrying rod extending between the proximal and distal ends of the endoscope sheath, with said rod terminating at a generally central location of the distal end of the therapeutic energy carrying optical fiber bundle, said spotter light path being oriented at the distal end to produce a visible spotter beam into the body cavity for illumination of a real light spot which is generally coincident with the predetermined location of the therapeutic radiation beam to visually locate the area of incidence of the therapeutic radiation beam in the body cavity.

2. The radiation endoscope as claimed in claim 1 wherein the endoscope is further provided at its proximal end with adjustable light filter means interposed in the therapeutic energy carrying path and the optical image transmitter, said optical filter means providing a variation of attenuation of the intensity of the therapeutic energy in inverse relationship with attenuation of the image passed through the optical image transmitter for protection of the eye of an observer.

3. In a radiation endoscope wherein an image transmitter extends from a distal end to a proximal end of the endoscope and an optical path is provided for delivering therapeutic radiation energy from the proximal end to the distal end, the improvement comprising
  an adjustable image light filter interposed at the proximal end of the endoscope in the image transmitter, and means coupled to the adjustable image light filter for effectively reducing the radiation energy in the radiation energy path to protect the eye of an operator when an image is being observed during therapeutic application of radiation energy.

4. The improved radiation endoscope as set forth in claim 3 wherein said means is a variable density radiation energy filter selected to attenuate radiation energy in the radiation path and wherein the variable radiation filter has a transmissivity which provides a variation of attenuation of the intensity of the therapeutic radiation energy in inverse relationship with attenuation of the adjustable image light filter.

5. The improved radiation endoscope as set forth in claim 3 wherein said means includes
  a radiation control signal generator coupled to the adjustable image light filter to generate a control signal whose value represents the desired magnitude of the radiation energy in the radiation path in correspondence with the transmissivity of the adjustable image light filter for eye protection.

6. The improved radiation endoscope as set forth in claim 4 wherein the image and radiation filters are formed of
  a filter and a carrier mounted in fixed relationship with each other and for rotation about a common axis, said filter being formed with variable density optical filter plates with density gradients oriented to provide opposite transmissivity in the radiation energy path and image transmitter as the carrier and filter are rotated.

7. The improved radiation endoscope as claimed in claim 6 wherein the filter is provided with slots curved about the common axis and wherein the variable density optical filter plates are mounted in said slots.

* * * * *